(12) United States Patent
Dumon D'Ayot et al.

(10) Patent No.: US 8,597,223 B2
(45) Date of Patent: Dec. 3, 2013

(54) CONTAINER FOR USE IN DIALYSIS

(75) Inventors: Francois Dumon D'Ayot, Lyons (FR); Thierry Dupin, Besseway (FR); Philippe Laffay, Fou les Lyon (FR); Thomas Graf, St. Jean des Vignes (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 10/493,447

(22) PCT Filed: Jul. 16, 2002

(86) PCT No.: PCT/EP02/07922
§ 371 (c)(1),
(2), (4) Date: Apr. 23, 2004

(87) PCT Pub. No.: WO03/035146
PCT Pub. Date: May 1, 2003

(65) Prior Publication Data
US 2004/0243094 A1  Dec. 2, 2004

(30) Foreign Application Priority Data

Oct. 23, 2001  (DE) .................................. 101 52 105

(51) Int. Cl.
*A61M 1/14* (2006.01)
*A61M 5/00* (2006.01)
*A61B 19/00* (2006.01)

(52) U.S. Cl.
USPC .......... 604/4.01; 604/403; 604/406; 604/408; 604/410; 604/416

(58) Field of Classification Search
USPC ......... 604/4.01, 6.16, 403–410; 128/DIG. 24; 383/35, 37–42, 67, 80, 81, 93, 94, 105, 383/106, 121, 123, 125, 127; 206/219, 222, 206/828; 222/92, 94, 129, 135, 206–212; 220/500
See application file for complete search history.

(56) References Cited

U.S. PATENT DOCUMENTS 3,517,816 A * 6/1970 Hoppen .................... 210/266
4,282,863 A * 8/1981 Beigler et al. ............. 604/262
4,396,382 A * 8/1983 Goldhaber ................. 604/28

(Continued)

FOREIGN PATENT DOCUMENTS

DE  691 20 264 T   2/1997
EP  0 475 825       3/1992

(Continued)

OTHER PUBLICATIONS

First Online dictionary reference on "bed," accessed Monday, Mar. 28, 2011. http://education.yahoo.com/reference/dictionary/entry/bed.*

(Continued)

*Primary Examiner* — Adam Marcetich
(74) *Attorney, Agent, or Firm* — Jacobson Holman PLLC

(57) ABSTRACT

A container for use in dialysis, containing a certain amount of a salt concentrate in the form of a powder, granules or tablets or mixtures thereof, having an inlet for the water and an outlet that is connectable to a dialysis machine. Both the inlet and the outlet are situated on one side of the container, and each includes a filter therein to prevent any undissolved salt concentrate from leaving the container.

29 Claims, 3 Drawing Sheets

(56) References Cited

U.S. PATENT DOCUMENTS

| | | | |
|---|---|---|---|
| 4,403,992 A * | 9/1983 | Bertellini et al. | 604/410 |
| 4,550,825 A * | 11/1985 | Sutryn et al. | 206/222 |
| 4,560,382 A * | 12/1985 | Isono | 604/408 |
| 4,608,043 A * | 8/1986 | Larkin | 604/87 |
| 4,610,684 A * | 9/1986 | Knox et al. | 604/416 |
| 4,795,265 A * | 1/1989 | Dahlberg et al. | 366/69 |
| 4,879,030 A * | 11/1989 | Stache | 210/238 |
| 5,304,130 A * | 4/1994 | Button et al. | 604/85 |
| 5,326,473 A * | 7/1994 | Lascombes et al. | 210/474 |
| 5,385,564 A * | 1/1995 | Slater et al. | 604/416 |
| 5,387,237 A | 2/1995 | Fournier et al. | |
| 5,431,496 A * | 7/1995 | Balteau et al. | 383/38 |
| 5,484,431 A * | 1/1996 | Scharf et al. | 604/416 |
| 5,490,848 A * | 2/1996 | Finley et al. | 604/403 |
| 5,616,305 A * | 4/1997 | Mathieu | 422/261 |
| 5,944,709 A * | 8/1999 | Barney et al. | 604/410 |
| 6,036,858 A * | 3/2000 | Carlsson et al. | 210/232 |
| 6,309,373 B1 * | 10/2001 | Shalwitz et al. | 604/85 |
| 6,375,974 B1 * | 4/2002 | Ito et al. | 424/434 |
| 6,407,070 B1 * | 6/2002 | Kai et al. | 514/23 |
| 6,428,505 B1 * | 8/2002 | Taylor | 604/80 |
| 6,527,738 B1 * | 3/2003 | Jones et al. | 604/84 |
| 6,605,214 B1 * | 8/2003 | Taylor | 210/232 |
| 7,244,247 B1 * | 7/2007 | Falciani et al. | 604/408 |
| 2002/0177837 A1 * | 11/2002 | Barnitz | 604/416 |

FOREIGN PATENT DOCUMENTS

| | | |
|---|---|---|
| EP | 0 484 751 | 5/1992 |
| EP | 0 665 026 | 8/1995 |
| FR | 2 766 797 | 2/1999 |
| JP | 07 299134 | 11/1995 |

OTHER PUBLICATIONS

Second Online dictionary reference on "bed," accessed Monday, Mar. 28, 2011. http://www.merriam-webster.com/dictionary/bed?show=0&t=1301328186.*

* cited by examiner

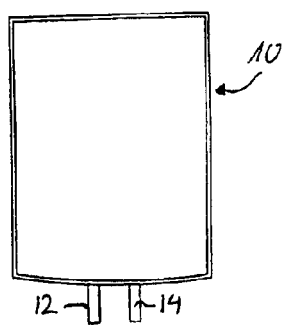
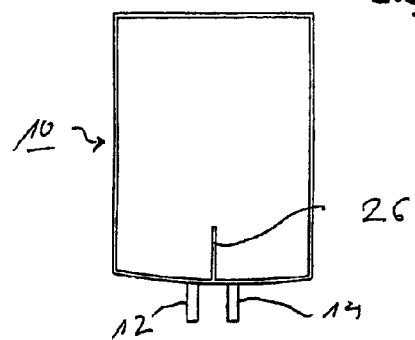
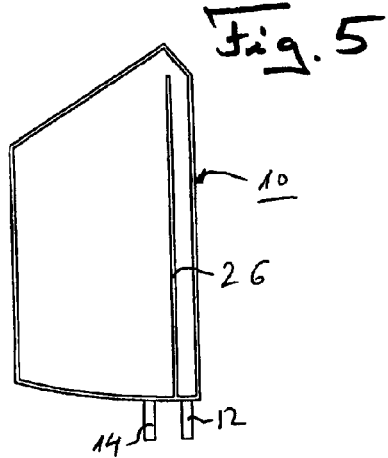
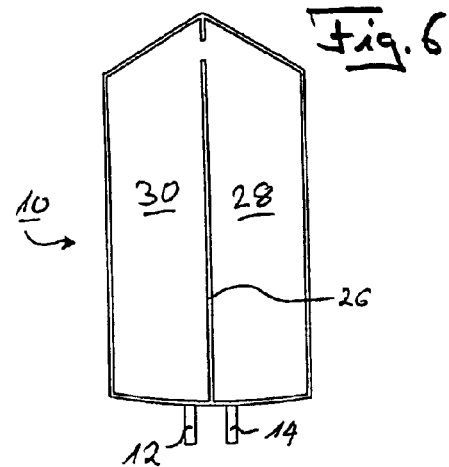
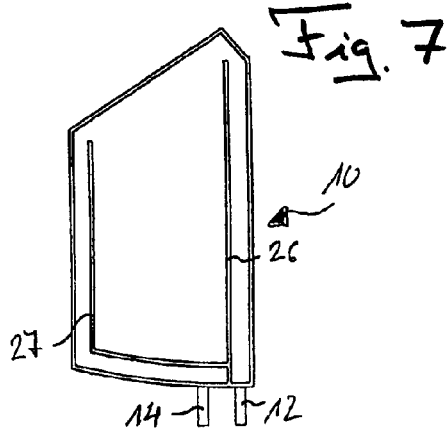
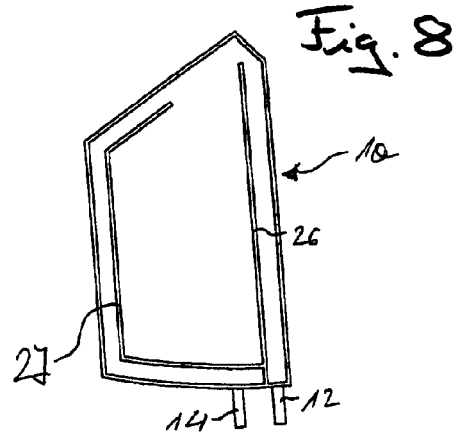

CONTAINER FOR USE IN DIALYSIS

This is a nationalization of PCT/EP02/07922 filed Jul. 16, 2002 and published in German.

BACKGROUND OF THE INVENTION

1. Field of the Invention

The present invention relates to a container for use in dialysis containing a certain amount of a salt concentrate in the form of powder, granules or tablets or mixtures thereof, having an inlet for water and an outlet that is connectable to a dialysis machine.

2. Description of the Related Art

In dialysis systems, it has previously been customary to prepare the dialysate needed for the dialysis process just before the dialysis session. To do so, the dialysate concentrate in solid form is placed in a container; the dialysate solids are usually in the form of powders, granules or tablets, i.e., pressed tablets of powder. To form the dialysate, the solid dialysate concentrate must be dissolved in water. To do so, the container with the solid dialysate concentrate is secured in the dialysis machine and the water in which the dialysate concentrate is to be dissolved is usually introduced into the container on one side and removed again on the opposite side. This results in the problem that the solution discharged is not saturated, so the composition of the dialysate varies.

U.S. Pat. No. 5,385,564 describes a solution which starts with the granular form of the dialysate concentrate in a container, with the water being introduced into the container through a connection. However, the water must first be introduced completely into the container and the finished dialysate is discharged again through the same opening in the container after appropriate dissolving of the concentrate in the water. Continuous operation is impossible with this solution.

SUMMARY OF THE INVENTION

The object of the present invention is to make available a container with which it is certain that the solution prepared for the dialysis session is saturated, even when using components having a very low solubility.

This object is achieved according to the present invention starting from a known container by the fact that both the inlet and the outlet are situated on one side of the container, preferably in the bottom area. It is essential here for both the inlet and outlet to be situated in proximity to the dialysis concentrate, which is in the form of solids. This ensures that fresh water will flow around the dialysate concentrate particles in solid form and contribute to the most rapid possible dissolving because of the resulting turbulent flow and development of eddies. Positioning the outlet on the same side as the inlet ensures that the liquid will have the longest possible dwell time in the dialysate concentrate, which is not yet dissolved, even in continuous operation, so that saturation of the solution can be achieved here even in the case of salts having a low solubility. Because of this arrangement, the differences in density can also be compensated.

Preferred embodiments of the present invention are briefly described as follows.

Accordingly, the container may advantageously be designed in the form of a bag which is formed by two films welded together, the inlet and outlet being formed in the bottom area, whereby the inlet and outlet are preferably designed in the form of connectors which are connectable to the dialysis machine.

Filters having a porosity of 50 µm to 500 µm are especially advantageously provided in both the inlet and outlet.

The container may have one or more partitions to form different areas in the interior, but the partitions are at least perforated so that an exchange of fluid between the individual regions is possible. In this variant, the fluid passes in a labyrinthine path through the container before reaching the outlet after starting from the inlet and flowing through the solid dialysate concentrate and partially dissolving same. With an appropriate configuration of the partitions, the inlet and outlet may also be situated outside of the bottom area if it is ensured that through an appropriate configuration of the partitions, the fresh liquid is guided through the sediment of dialysate concentrate which is made up of solids. In this container, the partitions can be produced especially easily if the container is made of a bag in which the side walls of the bag are welded together at appropriate locations where the partitions are to be formed.

The container may be used to particular advantage when the dialysate concentrate contains sodium bicarbonate or sodium chloride, among other ingredients.

These and other objects of the invention, as well as many of the intended advantages thereof, will become more readily apparent when reference is made to the following description taken in conjunction with the accompanying drawings.

BRIEF DESCRIPTION OF THE DRAWINGS

Additional details and advantages of this invention are explained in greater detail below on the basis of an exemplary embodiment depicted in the drawings, in which:

FIGS. 3-8 illustrate different embodiments of the present invention in a simplified sectional diagram.

DETAILED DESCRIPTION OF THE PREFERRED EMBODIMENTS

Figure 1:
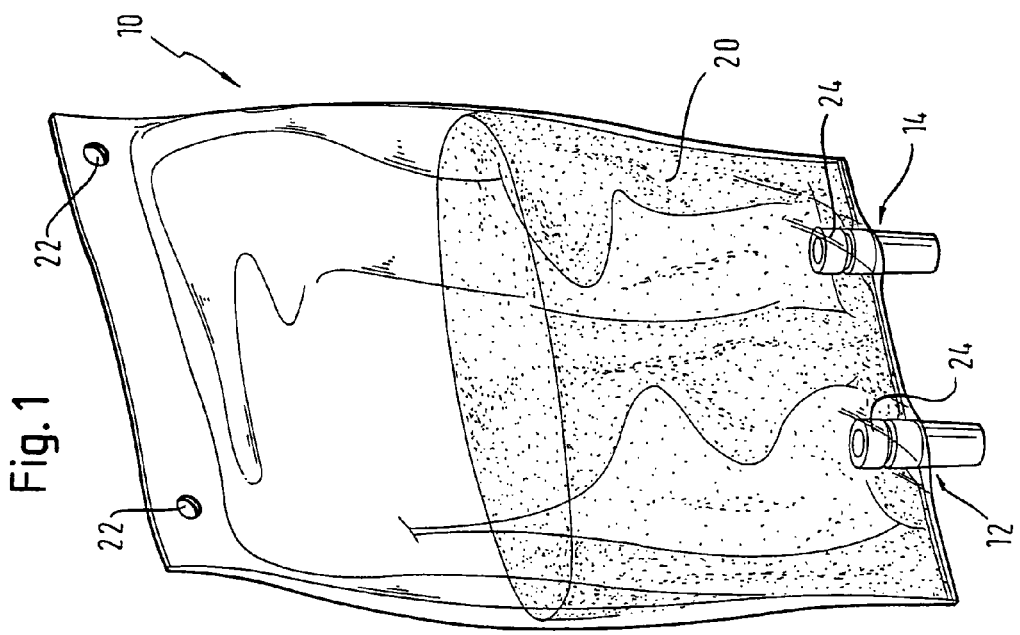
FIG. 1 is a schematic diagram of a first variant of the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

In the variant according to FIG. 1, the container 10 consists of a bag made of two plastic films welded together at the sides. In the bottom area of the bag 10, an inlet 12 and an outlet 14 are provided, these being designed as tubular connections in the exemplary embodiment depicted here, with the corresponding tubing ends 16, 18 (see FIG. 2a) being attachable thereto by pushing onto the connection. The lower part of the bag contains the dialysate concentrate 20 comprising of powder, granules or tablets and/or mixtures thereof. In the upper area, the bag 10 has two receptacle openings 22 by means of which these bags can be suspended. Filters 24 having a porosity of 50 µm to 500 µm that can be inserted into the tube are arranged in the inlet 12 and the outlet 14. These filters 24 are also shown in sectional view in FIG. 2a.

Figure 2:
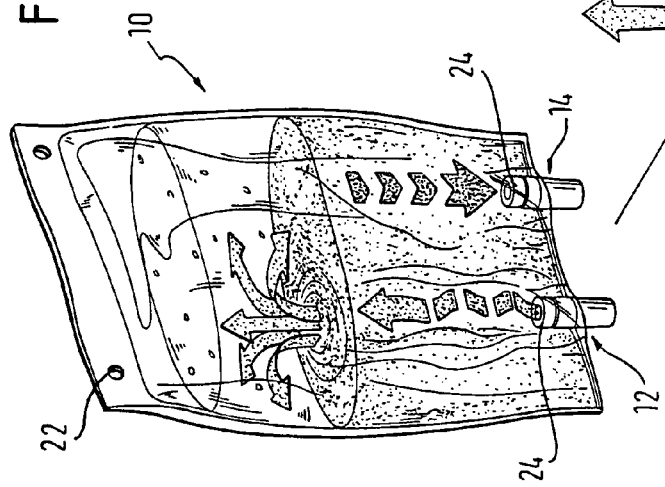
FIG. 2 and FIG. 2a present a graphic illustration of the introduction of water into a bag according to FIG. 1, partially enlarged.
Figure 2A:
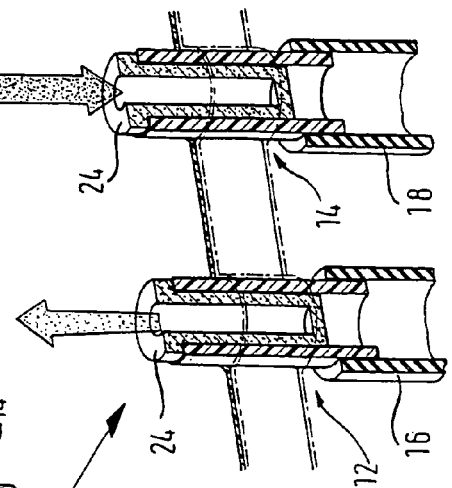

FIG. 2 shows the flow pattern of the water flowing in through the inlet 12. In particular, the arrows here indicate that fluid flows through the dialysate concentrate along a comparatively broader channel and therefore turbulence is created due to this flow and also due to the density differences between more and less concentrated solution. From the upper area of the bag, the water must again flow through the entire bed of dialysate concentrate to then be removed in saturated form through the outlet 14. The filters 24 prevent any undissolved dialysate concentrate from entering the tubing lines 16 and/or 18.

On the basis of FIGS. 3 through 8, the different variants of the inventive container 10, which is in the form of a bag here, can be explained. The bag shape is a simple embodiment but this shape is not necessarily stipulated according to the present invention.

FIG. 3 shows a section corresponding to the embodiment according to FIGS. 1 and 2. FIGS. 4 through 8 differ from this simplest of variants in that partitions 26 are provided here in the interior of the bag, forming different regions in the bag. This results in a labyrinthine passage of the fresh water through the bed of dialysate concentrate.

FIG. 4 shows the partition 26 between the inlet 12 and the outlet 14, serving here essentially to prevent a short-circuit flow between the inlet and the outlet. In the variant according to FIG. 5, two partial regions are created within the bag, these two partial regions being of very different sizes, although the inlet and outlet here are again shown in the lower region of the bag. Essentially, however, they could also be rotated by 180°. In this case, the inlet would be situated in the narrower region of the inlet. Due to the design of the partition, this ensures that fresh water is introduced into the region of the dialysate concentrate containing solids and passes through this concentrate before the saturated solution is then discharged from the outlet 14.

FIG. 6 shows two symmetrical chambers 28 and 30 formed by the partition 26.

FIG. 7 corresponds essentially to FIG. 5 and leads to a bag that is similarly usable. In this case an elongated chamber is formed merely by an additional partition 27 within the bag, thus defining the inlet in relation to the outlet 14. This chamber is designed to be even longer according to the diagram in FIG. 8. The variants according to FIGS. 5 through 8 each have bags which are shaped in a triangular shape toward one side. This is appropriate in particular when the bags are rotated by 180° in comparison with the diagram here, because then the undissolved dialysate concentrate collects in the region of the tip of the triangle, i.e., in the lowest region of the bag whereby here due to the corresponding design of the chambers formed by the partitions, this ensures that the liquid also flows through this region of the bag.

Figure 9:
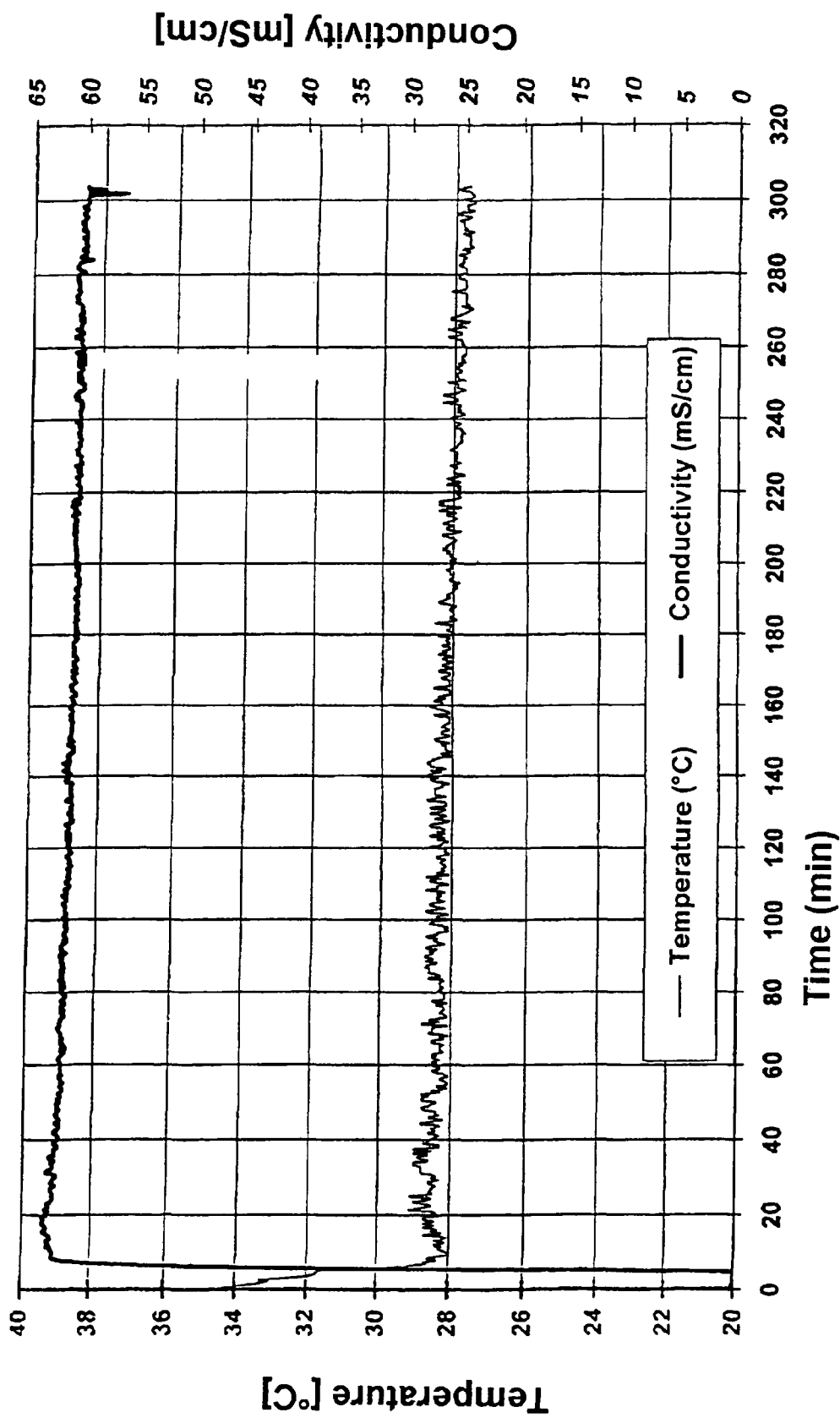
FIG. 9 is a diagram showing the temperature of the liquid as a function of time.

Finally, FIG. 9 shows a diagram which indicates that a constant saturation concentration can be achieved if a constant temperature is maintained during preparation of the dialysate. The saturation of the solution here is determined by measuring the conductivity. A constant conductivity of approximately 60 mS/cm is also measured here at a constant temperature of slightly more than 28° C., with the dialysate here being measured over a suitable period of time at the outlet 14 in an arrangement according to that shown in FIG. 1.

The foregoing descriptions and drawings should be considered as illustrative only of the principles of the invention. The invention may be configured in a variety of shapes and sizes and is not limited by the dimensions of the preferred embodiment. Numerous applications of the present invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A device for use in dialysis comprising the combination of:
   i. a container having an interior area in which solid form salt concentrate is mixed with water, and
   ii. a bed of solid form salt concentrate contained in said interior area of said container prior to use of said device so that only water is introduced into said container for mixture with the salt concentrate in the interior area when the device is used;
   said container having an inlet for water and an outlet that is connectable to a dialysis machine, said inlet and said outlet being located adjacent one another and both the inlet and the outlet being positioned in direct proximity to said bed of solid form salt concentrate contained in said interior area of said container and each having a respective filter therein to prevent any undissolved salt concentrate from leaving the container,
   said device being configured so that water entering the interior area of the container through the inlet is saturated in said container during continuous operation by said water passing through an entire bed of said salt concentrate a first time after incoming through said inlet as a first flow in a first direction and passing through an entire bed of said salt concentrate a second time to mix with said salt concentrate before exiting said container through said outlet as a second flow in a second direction counter current to said first direction, said first and second flows occurring concurrently and being in direct proximity to one another inside the container so that said flows themselves create a turbulent flow around the salt concentrate for saturation of said water.

2. The device according to claim 1, wherein the container includes a flexible bag defining a single chamber.

3. The device according to claim 2, wherein said inlet and said outlet include connectors arranged in a bottom side of the bag when the bag is in use, access openings to said interior area of said container being limited to only said inlet, through which water enters the container, and said outlet, through which water saturated with salt concentrate exits the container.

4. The device according to claim 3, wherein said water after incoming through said inlet forms a first flow in an upward direction and before exiting said container through said outlet forms a second flow in a downward direction.

5. The device according to claim 1, wherein each of said filters has a porosity of from about 50 µm to 500 µm.

6. The device according to claim 1, wherein an interior of said bag includes at least one partition forming different regions in the container, said partition having perforations that allow a fluid exchange between said regions.

7. The device according to claim 6, wherein the partition includes side walls of the bag welded together.

8. The device according to claim 1, wherein said salt concentrate includes bicarbonate.

9. The device according to claim 1, wherein said salt concentrate includes sodium chloride.

10. The device according to claim 1, wherein said salt concentrate is in a form including powder, granules, tablets or mixtures thereof.

11. The device according to claim 1, wherein said salt concentrate remains at least partly in solid form during said continuous operation.

12. The device according to claim 1, wherein said device is configured and used for the continuous preparation of a fluid for dialysis which is saturated with the salts contained in said salt concentrate.

13. The device according to claim 1, in combination with a dialysis machine.

14. A device for use in dialysis comprising a container and a single bed of salt concentrate solids contained within said container prior to use of said device, said container having an inlet for water and an outlet that is connectable to a dialysis machine, both the inlet and the outlet being located adjacent one another in a lower side of the container and both in direct proximity to a lower side of said bed of salt concentrate solids, which solids are located in a lower part of said container when the container is in use, both the inlet and the outlet having a respective filter therein to prevent undissolved salt concentrate solids from leaving the container, said device being configured so that, during continuous operation, at least a part of said bed of salt concentrate solids remains undissolved and water is saturated in said container by said water first passing from the lower side of said bed upwardly through said undissolved part of said bed of salt concentrate a first time after incoming through said inlet and by second passing in a downward direction through said undissolved part of said bed of salt concentrate a second time before exiting said container through said outlet, at least part of said undissolved part being in direct contact with said outlet port to ensure said water passes through said undissolved part a second time.

15. The device according to claim 14, wherein the container is a flexible-walled bag having a single chamber, an interior of said container being accessible only through said inlet, through which water enters the container, and through said outlet, through which water saturated with salt concentrate exits the container.

16. The device according to claim 14, wherein said device is configured and used for the continuous preparation of a fluid for dialysis which is saturated with the salts contained in said salt concentrate.

17. The device according to claim 14, in combination with a dialysis machine.

18. A container for use in dialysis, said container having a bed of solid form salt concentrate contained within its interior prior to use, said container comprising:

an inlet for water and an outlet that is connectable to a dialysis machine, said inlet and said outlet being located adjacent to one another and both the inlet and the outlet being positioned in direct proximity to said bed of solid form salt concentrate in said container interior, each of said inlet and outlet including a filter to prevent any undissolved salt concentrate from leaving the container, the interior of said container being accessible only through said inlet, through which water enters the container, and through said outlet, through which water saturated with salt concentrate exits the container;

said container being configured so that water is saturated in said container during continuous operation by said water passing through an entire bed of salt concentrate a first time after incoming through said inlet as a first flow in a first direction and passing through an entire bed of salt concentrate a second time before exiting said container through said outlet as a second flow in a second direction counter current to said first direction, said first and second flows occurring concurrently and being in direct proximity to one another inside the container so that said flows themselves create a turbulent flow around the salt concentrate for saturation of said water.

19. The container according to claim 18, wherein the container is a flexible bag defining a single chamber.

20. The container according to claim 19, wherein said inlet and said outlet include connectors arranged in a bottom side of the bag when the bag is in use.

21. The container according to claim 18, wherein each of said filters has a porosity of from about 50 µm to 500 µm.

22. The container according to claim 18, wherein the container is a flexible bag and an interior of said bag includes at least one partition forming different regions in the container, said partition having perforations that allow a fluid exchange between said regions.

23. The container according to claim 22, wherein the partition includes side walls of the bag welded together.

24. The container according to claim 18, wherein said salt concentrate include bicarbonate.

25. The container according to claim 18, wherein said salt concentrate includes sodium chloride.

26. The container according to claim 18, wherein said salt concentrate is in a form including powder, granulates, tablets or mixtures thereof.

27. The container according to claim 18, wherein said salt concentrate remains at least partly in solid form during said continuous operation.

28. The container according to claim 18, wherein said container is configured and used for the continuous preparation of a fluid for dialysis which is saturated with the salts contained in said salt concentrate.

29. The container according to claim 18, in combination with a dialysis machine.

* * * * *